(12) United States Patent
Lanphear et al.

(10) Patent No.: US 12,299,388 B2
(45) Date of Patent: May 13, 2025

(54) SYSTEM AND METHOD FOR AUTOMATED PATIENT INTERACTION

(71) Applicant: 98point6 Inc., Seattle, WA (US)

(72) Inventors: Damon Lanphear, Vashon Island, WA (US); Keith Trnka, Seattle, WA (US); Robbie Schwietzer, Kirkland, WA (US)

(73) Assignee: 98point6 Technologies Inc., Seattle, WA (US)

( * ) Notice: Subject to any disclaimer, the term of this patent is extended or adjusted under 35 U.S.C. 154(b) by 0 days.

(21) Appl. No.: 18/244,352

(22) Filed: Sep. 11, 2023

(65) Prior Publication Data

US 2023/0419029 A1 Dec. 28, 2023

Related U.S. Application Data

(63) Continuation of application No. 16/685,060, filed on Nov. 15, 2019, now Pat. No. 11,914,953.

(51) Int. Cl.
*G06F 40/205* (2020.01)
*G06F 40/30* (2020.01)
(Continued)

(52) U.S. Cl.
CPC ............ *G06F 40/205* (2020.01); *G06F 40/30* (2020.01); *G06N 3/02* (2013.01); *G16H 10/60* (2018.01); *G16H 50/20* (2018.01)

(58) Field of Classification Search
CPC ...... G06F 40/205; G06F 40/30; G06F 40/284; G06F 16/3329; G06N 3/02; G06N 3/045;
(Continued)

(56) References Cited

U.S. PATENT DOCUMENTS 8,060,376 B2 * 11/2011 Horner .................. G16H 10/60
705/2
10,938,755 B1 * 3/2021 MacMillin .............. G06F 9/542
(Continued)

FOREIGN PATENT DOCUMENTS

EP     3216003 A1    9/2017
EP     3218891 A1    9/2017
(Continued)

OTHER PUBLICATIONS

Cranshaw et al., "Calendar.help: Designing a Workflow-Based Scheduling Agent with Humans in the Loop", Proceeding of the 2017 CHI Conference on Human Factors in Computing Systems—CHI '17, 2017, pp. 2382-2393.
(Continued)

*Primary Examiner* — Michael Colucci
(74) *Attorney, Agent, or Firm* — The Webb Law Firm

(57) ABSTRACT

Provided is a system and method for automated patient interaction. The method includes parsing a patient complaint comprising a plurality of words, determining a subset of patient queries from a plurality of patient queries based on the patient complaint and patient data, communicating the subset of patient queries to a first computing device; receiving, from the first computing device, responses to at least a portion of the subset of patient queries; generating output data based on the subset of patient queries and the responses; communicating the output data to a second computing device; receiving, from the second computing device, a user input corresponding to at least one patient query of the subset of patient queries; and training, based on the user input, at least one machine-learning algorithm configured to output at least one patient query based on at least one of the patient complaint and a subsequent patient complaint.

17 Claims, 8 Drawing Sheets

(51) Int. Cl.
  *G06N 3/02* (2006.01)
  *G16H 10/60* (2018.01)
  *G16H 50/20* (2018.01)

(58) Field of Classification Search
  CPC ............ G06N 5/01; G06N 3/08; G06N 20/10;
      G06N 20/20; G16H 10/60; G16H 50/20;
      G16H 10/20; G16H 80/00
  See application file for complete search history.

(56) References Cited

U.S. PATENT DOCUMENTS

| | | | |
|---|---|---|---|
| 10,943,407 B1* | 3/2021 | Morgan | G16H 15/00 |
| 11,410,761 B2* | 8/2022 | Kivatinos | G16H 10/60 |
| 2008/0015418 A1* | 1/2008 | Jarrell | G16H 70/20 |
| | | | 600/300 |
| 2009/0327297 A1* | 12/2009 | Deobhakta | G16H 10/60 |
| | | | 715/764 |
| 2013/0085780 A1* | 4/2013 | Braunstein | G16H 10/60 |
| | | | 705/3 |
| 2014/0379379 A1 | 12/2014 | Janevski et al. | |
| 2015/0332021 A1 | 11/2015 | Godla | |
| 2016/0098542 A1 | 4/2016 | Costantini et al. | |
| 2016/0210442 A1 | 7/2016 | Ethington et al. | |
| 2016/0232299 A1 | 8/2016 | Sklar et al. | |
| 2016/0335399 A1 | 11/2016 | Vancho | |
| 2017/0098051 A1 | 4/2017 | Balram | |
| 2017/0249600 A1 | 8/2017 | Cranshaw et al. | |
| 2017/0262609 A1 | 9/2017 | Perlroth et al. | |
| 2018/0004915 A1 | 1/2018 | Talbot et al. | |
| 2018/0089381 A1* | 3/2018 | Allen | G16H 70/20 |
| 2018/0096735 A1 | 4/2018 | Pappu | |
| 2018/0096738 A1* | 4/2018 | Moturu | G16H 50/20 |
| 2018/0330802 A1 | 11/2018 | Sharifi Sedeh et al. | |
| 2019/0087543 A1 | 3/2019 | Abou Mahmoud et al. | |
| 2019/0095590 A1 | 3/2019 | Knoop et al. | |
| 2019/0180875 A1 | 6/2019 | Gagne et al. | |
| 2019/0189251 A1* | 6/2019 | Horiuchi | A61B 5/16 |
| 2019/0198150 A1* | 6/2019 | Kang | G16H 50/70 |
| 2019/0246968 A1* | 8/2019 | Matic | G16H 40/67 |
| 2019/0326022 A1* | 10/2019 | El-kalliny | G16H 80/00 |
| 2020/0118680 A1* | 4/2020 | Rao | G16H 80/00 |
| 2020/0135175 A1* | 4/2020 | Katz | G10L 15/30 |
| 2020/0243178 A1* | 7/2020 | Sweeney | G16H 70/60 |
| 2020/0335187 A1* | 10/2020 | Lefkofsky | G06F 3/0481 |
| 2021/0057078 A1* | 2/2021 | Suzuki | G09B 19/00 |
| 2021/0358637 A1* | 11/2021 | Devdas | G16H 40/67 |
| 2022/0000374 A1* | 1/2022 | Galgalikar | A61B 5/333 |

FOREIGN PATENT DOCUMENTS

| | | |
|---|---|---|
| WO | 2018220565 A1 | 12/2018 |
| WO | 2019060288 A1 | 3/2019 |

OTHER PUBLICATIONS

Solon, "The rise of 'pseudo-AI': how tech firms quietly use humans to do bots' work", 2018, 5 pages, retrieved from https://www.theguardian.com/technology/2018/jul/06/artificial-intelligence-ai-humans-bots-tech-companies.

Yang et al., "Mastering the Dungeon: Grounded Language Learning by Mechanical Turker Descent", arXiv:1711.07950v3, Apr. 16, 2018, pp. 1-16.

Ibrahim et al., "IWSMD: An Intelligent Web Service based Medical Diagnosis System", INFOS2008, Faculty of Computers & Information—Cairo University, 2008, pp. 6-14.

* cited by examiner

Chief Complaint:
"I've had sinus pain for two weeks"

Age/Sex:
26 / Female

Preliminary questions

Which of these STORY questions should be asked?
- ● Please tell me more about your current symptoms.
- ○ Can you tell me how it started and how your symptoms have changed over time?
- ○ Overall are your symptoms getting better or worse?
- ○ Do you have any other symptoms not mentioned so far that are bothering you?
- ● When did it start?
- ○ Have you had something like this before?
- ○ Anyone else around you with a similar illness?
- ○ Have you tried anything for it and did it help?
- ○ Have you taken any antibiotics in the last month or had any changes in your medications?
- ● How long have you had this?
- ○ Have you had any lightheadedness?
- ● Any muscle aches?
- ○ Can you send a picture?
- ○ How often do you take time off work for this?
- ○ Left or right?

| — | __Fever/Temperature Questions__ |

Which of these questions should be asked?

☐ Have you had any fevers?

☐ Have you measured your temperature?

☐ Have you had the sweats or chills?

| + | __Women's Health Questions__ |

| + | __Urinary/UTI Questions__ |

| + | __Genital Infection Questions__ |

| + | __Respiratory Questions__ (recommended) |

| + | __Asthma Questions__ |

| + | __Vision Questions__ |

| + | __Throat Questions__ |

| Chief complaint | Labels | |
|---|---|---|
| I believe I might have a vaginal infection... _504_ | Medication refill<br>Acute symptoms<br>Chronic symptoms<br>General question<br>Seeking second opinion<br>Other _506_ | |

| Question Bot question | Patient answer | Labels |
|---|---|---|
| Have you had something like this before? _508_ | Long time ago _510_ | Valuable<br>Repeat<br>Irrelevant<br>Not valuable _512_ |
| Have you tried anything for it and did it help? | Yes, vagisil creme | Valuable<br>Repeat<br>Irrelevant<br>Not valuable |
| Have you had any fevers? | No | Valuable<br>Repeat<br>Irrelevant<br>Not valuable |
| Could you describe your recent sexual history? Please note any risk factors for sexually transmitted infections such as: a new sex partner in the last few months, multiple partners, or a partner... | None | Valuable<br>Repeat<br>Irrelevant<br>Not valuable |

| Clinician question | Patient answer | Labels |
|---|---|---|
| I see that you are concerned about a vaginal infection. Are you thinking a yeast type infection? _514_ | I believe so _516_ | Medical interview ends<br>Unique question (NOT in annotation library)<br>Profile related question<br>Repeat (QB already asked this)<br>Annotation library question<br>Statement, not a question _518_ |
| What specific symptoms are you having? | Itch, a little bit of discharge, no odor... | Medical interview ends<br>Unique question (NOT in annotation library)<br>Profile related question<br>Repeat (QB already asked this) |

FIG. 5    _502_

{"text": "I have a cough and a fever"}

| cough | have | don't | fever | ... | allergies |
|-------|------|-------|-------|-----|-----------|
| 1 | 1 | 0 | 1 | ... | 0 |

FIG. 6    602

| When did it start? | Does anything make it worse? | Have you measured your temperature? | Are your ears ringing? | ... | What condition do you take this medication for? |
|---|---|---|---|---|---|
| 1 | 0 | 0 | 1 | | 0 |

FIG. 7    702

SYSTEM AND METHOD FOR AUTOMATED PATIENT INTERACTION

CROSS REFERENCE TO RELATED APPLICATION

This application is a continuation application of U.S. patent application Ser. No. 16/685,060, filed on Nov. 15, 2019, the disclosure of which is hereby incorporated by reference in its entirety.

BACKGROUND

1. Field

This disclosure relates generally to patient interaction and, in non-limiting embodiments, to systems, methods, and computer-program products for automatically interacting with patients.

2. Technical Considerations

Patients seeking medical treatment or advice must often wait for long periods of time to consult with a healthcare professional. For remote consultations through respective computing devices operated by a patient and healthcare professional, it is desirable to automate information gathering steps, such as posing questions to the patient, to reduce the amount of time spent by a relevant healthcare professional. It is also desirable to reduce the number of queries posed to the patient to ensure a quick and efficient patient interaction, to keep the patient engaged, to efficiently use computing resources, and to optimize the information being gathered to allow the healthcare professional to make an informed diagnosis or recommendation.

SUMMARY

According to non-limiting embodiments or aspects, provided is a computer-implemented method for automated patient interaction, comprising: parsing, with at least one processor, a patient complaint comprising a plurality of words relating to a health of a patient; determining, with at least one processor, a subset of patient queries from a plurality of patient queries stored in a patient query database based on the patient complaint and patient data; communicating the subset of patient queries to a first computing device; receiving, from the first computing device, responses to at least a portion of the subset of patient queries; generating, with at least one processor, output data based on the subset of patient queries and the responses; communicating the output data to a second computing device; receiving, from the second computing device, a user input corresponding to at least one patient query of the subset of patient queries; and training, with at least one processor and based on the user input, at least one machine-learning algorithm configured to output at least one patient query based on at least one of the patient complaint and a subsequent patient complaint.

In non-limiting embodiments, the plurality of patient queries is arranged in at least one data structure, and wherein communicating the subset of patient queries to the first computing device and receiving the responses to the at least a portion of the subset of patient queries comprises: communicating at least one query of the subset of patient queries to the first computing device; receiving a response to the at least one query from the first computing device; selecting a next query of the subset of patient queries based on the response; communicating the next query to the first computing device; and receiving a next response to the next query from the first computing devices. In non-limiting embodiments, the user input comprises removing at least one patient query from the subset of patient queries. In non-limiting embodiments, the user input comprises adding at least one query to the subset of patient queries from the plurality of patient queries. In non-limiting embodiments, the user input comprises prioritizing at least one query of the subset of patient queries with respect to at least one other query of the subset of patient queries. In non-limiting embodiments, communicating the subset of patient queries is performed by a chat bot application configured to interact with the patient via voice and/or text. In non-limiting embodiments, the patient data comprises at least one of a gender and an age. In non-limiting embodiments, determining the subset of patient queries is based further on at least one response received from the first computing device to at least one initial query determined based on the patient complaint.

In non-limiting embodiments, the computer-implemented method further comprises: after communicating the output data to the second computing device, facilitating voice and/or text communication between an operator of the second computing device and the patient using the first computing device. In non-limiting embodiments, the at least one machine-learning algorithm applies at least one model to the patient complaint and the patient data, the method further comprising: generating training data based on a plurality of patient complaints and training input data corresponding to the plurality of patient complaints; and training the at least one model based on the training data. In non-limiting embodiments, the computer-implemented method further comprises: communicating the plurality of patient complaints and the plurality of patient queries to a third computing device; and receiving, from the third computing device, a selected subset of patient queries from the plurality of patient queries, the training input data comprises the selected subset of patient queries. In non-limiting embodiments, the user input received from the second computing device comprises the voice and/or text communication. In non-limiting embodiments, the at least one machine-learning algorithm applies a neural network to the patient complaint and the patient data. In non-limiting embodiments, the neural network is based on word embeddings.

According to non-limiting embodiments or aspects, provided is a system for automated patient interaction, comprising: at least one data storage device comprising a plurality of patient queries; and at least one processor in communication with the at least one data storage device, the at least one processor programmed or configured to: parse a patient complaint comprising a plurality of words relating to a health of a patient; determine a subset of patient queries from the plurality of patient queries based on the patient complaint and patient data; communicate the subset of patient queries to a first computing device; receive, from the first computing device, responses to at least a portion of the subset of patient queries; generate output data based on the subset of patient queries and the responses; communicate the output data to a second computing device; receive, from the second computing device, user input corresponding to at least one patient query of the subset of patient queries; and train at least one machine-learning algorithm based on the user input, the at least one machine-learning algorithm configured to output at least one patient query based on at least one of the patient complaint and a subsequent patient complaint.

In non-limiting embodiments, the plurality of patient queries is arranged in at least one data structure, and wherein communicating the subset of patient queries to the first computing device and receiving the responses to the at least a portion of the subset of patient queries comprises: communicating at least one query of the subset of patient queries to the first computing device; receiving a response to the at least one query from the first computing device; selecting a next query of the subset of patient queries based on the response; communicating the next query to the first computing device; and receiving a next response to the next query from the first computing devices. In non-limiting embodiments, the user input comprises removing at least one patient query from the subset of patient queries. In non-limiting embodiments, the user input comprises adding at least one query to the subset of patient queries from the plurality of patient queries. In non-limiting embodiments, the user input comprises prioritizing at least one query of the subset of patient queries with respect to at least one other query of the subset of patient queries. In non-limiting embodiments, wherein communicating the subset of patient queries is performed by a chat bot application configured to interact with the patient via voice and/or text. In non-limiting embodiments, the patient data comprises at least one of a gender and an age. In non-limiting embodiments, wherein determining the subset of patient queries is based further on at least one response received from the first computing device to at least one initial query determined based on the patient complaint.

In non-limiting embodiments, the at least one processor is further programmed or configured to: after communicating the output data to the second computing device, facilitate voice and/or text communication between an operator of the second computing device and the patient using the first computing device. In non-limiting embodiments, the user input received from the second computing device comprises the voice and/or text communication. In non-limiting embodiments, the at least one machine-learning algorithm applies a neural network to the patient complaint and the patient data. In non-limiting embodiments, the neural network is based on word embeddings. In non-limiting embodiments, the at least one machine-learning algorithm applies at least one model to the patient complaint and the patient data, and the at least one processor is further programmed or configured to: generate training data based on a plurality of patient complaints and training input data corresponding to the plurality of patient complaints; and train the at least one model based on the training data. In non-limiting embodiments, the at least one processor is further programmed or configured to: communicate the plurality of patient complaints and the plurality of patient queries to a third computing device; and receive, from the third computing device, a selected subset of patient queries from the plurality of patient queries, the training input data comprises the selected subset of patient queries.

According to non-limiting embodiments or aspects, provided is a computer program product for automated patient interaction, comprising at least one non-transitory computer-readable medium including program instructions that, when executed by at least one processor, cause the at least one processor to: parse a patient complaint comprising a plurality of words relating to a health of a patient; determine a subset of patient queries from a plurality of patient queries based on the patient complaint and patient data; communicate the subset of patient queries to a first computing device; receive, from the first computing device, responses to at least a portion of the subset of patient queries; generate output data based on the subset of patient queries and the responses; communicate the output data to a second computing device; receive, from the second computing device, user input corresponding to at least one patient query of the subset of patient queries; and train at least one machine-learning algorithm based on the user input, the at least one machine-learning algorithm configured to output at least one patient query based on at least one of the patient complaint and a subsequent patient complaint.

According to non-limiting embodiments or aspects, provided is a computer-implemented method for automated patient interaction, comprising: parsing, with at least one processor, a patient complaint comprising a plurality of words relating to a health of a patient; automatically interacting, with at least one processor and based on at least one machine-learning algorithm, with an operator of a first computing device by communicating a subset of patient queries to the first computing device and receiving responses to at least a portion of the subset of queries from the first computing device, the subset of queries selected from a plurality of patient queries; generating, with at least one processor, output data based on the responses; communicating the output data to a second computing device; receiving, from the second computing device, a user input corresponding to at least one patient query of the subset of patient queries; and training, with at least one processor, the at least one machine-learning algorithm based on the user input.

According to non-limiting embodiments or aspects, provided is a system for automated patient interaction, comprising: at least one data storage device comprising a plurality of patient queries; and at least one processor in communication with the at least one data storage device, the at least one processor programmed or configured to: parse a patient complaint comprising a plurality of words relating to a health of a patient; automatically interact, based on at least one machine-learning algorithm, with an operator of a first computing device by communicating a subset of patient queries to the first computing device and receiving responses to at least a portion of the subset of queries from the first computing device, the subset of queries selected from the plurality of patient queries; generate output data based on the responses; communicate the output data to a second computing device; receive, from the second computing device, a user input corresponding to at least one patient query of the subset of patient queries; and train the at least one machine-learning algorithm based on the user input.

According to non-limiting embodiments or aspects, provided is a computer program product for automated patient interaction, comprising at least one non-transitory computer-readable medium including program instructions that, when executed by at least one processor, cause the at least one processor to: parse a patient complaint comprising a plurality of words relating to a health of a patient; automatically interact, based on at least one machine-learning algorithm, with an operator of a first computing device by communicating a subset of patient queries to the first computing device and receiving responses to at least a portion of the subset of queries from the first computing device, the subset of queries selected from a plurality of patient queries; generate output data based on the responses; communicate the output data to a second computing device; receive, from the second computing device, a user input corresponding to at least one patient query of the subset of patient queries; and train the at least one machine-learning algorithm based on the user input.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying figures, in which:

FIGS. 4A and 4B illustrate graphical user interfaces for use in a system for automated patient interaction according to a non-limiting embodiment;

FIG. 5 illustrates another graphical user interface for use in a system for automated patient interaction according to a non-limiting embodiment;

FIG. 6 illustrates input data for use in a system for automated patient interaction according to a non-limiting embodiment;

FIG. 7 illustrates output data for use in a system for automated patient interaction according to a non-limiting embodiment;

DETAILED DESCRIPTION

Figure 1:
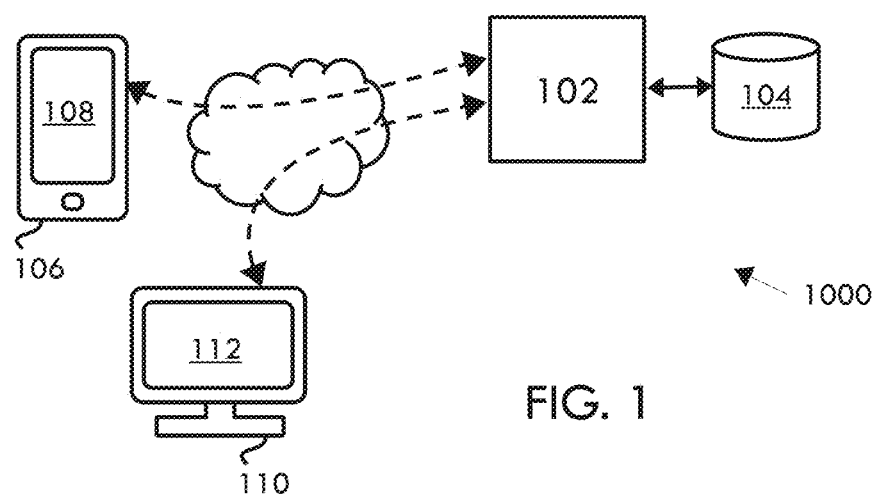
FIG. 1 illustrates a system for automated patient interaction according to a non-limiting embodiment.

It is to be understood that the embodiments may assume various alternative variations and step sequences, except where expressly specified to the contrary. It is also to be understood that the specific devices and processes described in the following specification, are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Further, the phrase "based on" is intended to mean "based at least partially on" unless explicitly stated otherwise.

As used herein, the term "communication" may refer to the reception, receipt, transmission, transfer, provision, and/or the like of data (e.g., information, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit processes information received from the first unit and communicates the processed information to the second unit.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. As an example, a mobile device may include a cellular phone (e.g., a smartphone or standard cellular phone), a portable computer, a wearable device (e.g., watches, glasses, lenses, clothing, and/or the like), a personal digital assistant (PDA), and/or other like devices. A computing device may also be a desktop computer or other form of non-mobile computer.

As used herein, the term "server computer" may refer to or include one or more computing devices that are operated by or facilitate communication and processing for multiple parties in a network environment, such as the Internet, although it will be appreciated that communication may be facilitated over one or more public or private network environments and that various other arrangements are possible. Further, multiple computing devices (e.g., server computers, mobile devices, etc.) directly or indirectly communicating in the network environment may constitute a "system." Reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

As used herein, the term "application programming interface" (API) may refer to computer code that allows communication between different systems or (hardware and/or software) components of systems. For example, an API may include function calls, functions, subroutines, communication protocols, fields, and/or the like usable and/or accessible by other systems or other (hardware and/or software) components of systems. As used herein, the term "user interface" or "graphical user interface" refers to a generated display, such as one or more graphical user interfaces (GUIs) with which a user may interact, either directly or indirectly (e.g., through a keyboard, mouse, touchscreen, etc.).

Non-limiting embodiments are directed to a system and method for automated patient interaction to provide relevant information to a healthcare team during an automated interaction with a patient conducted with a chat engine. Machine-learning techniques are used to parse a patient complaint and to select a subset of queries from a database of queries based on a complaint, thereby minimizing the number of queries being asked to the patient to elicit medically-relevant information for diagnosis, alerting, and/or triaging the patient. By reducing the number of queries being asked, computational resources and the respective individuals' time are used more efficiently. Non-limiting embodiments may be used for screening incoming patients, outpatient monitoring, selecting patients for clinical trials, and/or the like.

FIG. 1 shows a system 1000 for automated patient interaction according to a non-limiting embodiment. The system 1000 includes a server computer 102, which may be a computing device operating in a network environment. The server computer 102 may be in communication with one or more data storage devices through local and/or remote communication paths. In the example shown, the server computer 102 is in local communication with a query database 104 including query data stored on a first data storage device. The query data may include a plurality of queries (e.g., questions, prompts, choices, and/or the like) for eliciting information from a patient. The server computer 102 is also in communication with a first computing device 106 operated by a patient or another user on behalf of a patient. The first computing device 106 may include a mobile device or any other type of computing device and may display one or more GUIs 108 for facilitating patient interaction. The first computing device 106 may communicate with the server computer 102 through a mobile application, through a web browser, and/or the like. In non-limiting embodiments, communication between the first computing device 106 and the server computer 102 may be facilitated through one or more APIs, although various communication techniques may be used.

With continued reference to FIG. 1, the server computer 102 is also in communication with a second computing device 110 operated by a clinician, such as a doctor, nurse, therapist, individual acting on behalf of such healthcare professionals, and/or the like. The second computing device 110 may include a laptop computer, desktop computer, mobile device, and/or any other type of computing device and may display one or more GUIs 112 for facilitating clinician interaction. The second computing device 110 may communicate with the server computer 102 through an application, through a web browser, and/or the like. In non-limiting embodiments, communication between the second computing device 110 and the server computer 102 may be facilitated by one or more APIs, although various communication techniques may be used.

Still referring to FIG. 1, in non-limiting embodiments, the server computer 102 automatically interacts with the first computing device 106 using a subset of queries selected from the query database 104. As an example, in response to a complaint and patient data communicated from the first computing device 106, the server computer 102 may determine a subset of queries from a plurality of queries in the query database 104 to present to the operator of the first computing device through the GUI 108 The server computer 102 may interact with the operator of the first computing device 106 by presenting further queries based on responses received from the first computing device 106, thereby facilitating an automated interactive conversation in which the responses to the queries are used to select new queries and/or to collect patient data for later analysis. During or after the automated interaction, a clinician or other user operating the second computing device 110 may begin communicating with the operator (e.g., patient) of the first computing device 106. In some examples, the transition from an automated chat interaction to a human-controlled communication with an operator of the second computing device 110 may occur automatically or, in other examples, may occur in response to an input from the operator of the second computing device 110 (e.g., by selecting a button or the like). In some examples, the transition from an automated chat interaction to a human-controlled communication with an operator of the second computing device 110 may be transparent to the user or, in other examples, may be explicitly indicated. In this manner, the medical interview process to collect relevant information is automated, saving valuable clinician time and resources. The clinician is then involved after such an automated process to ask follow-up queries, communicate with the patient, and provide treatment or advice to the patient.

Figure 2:
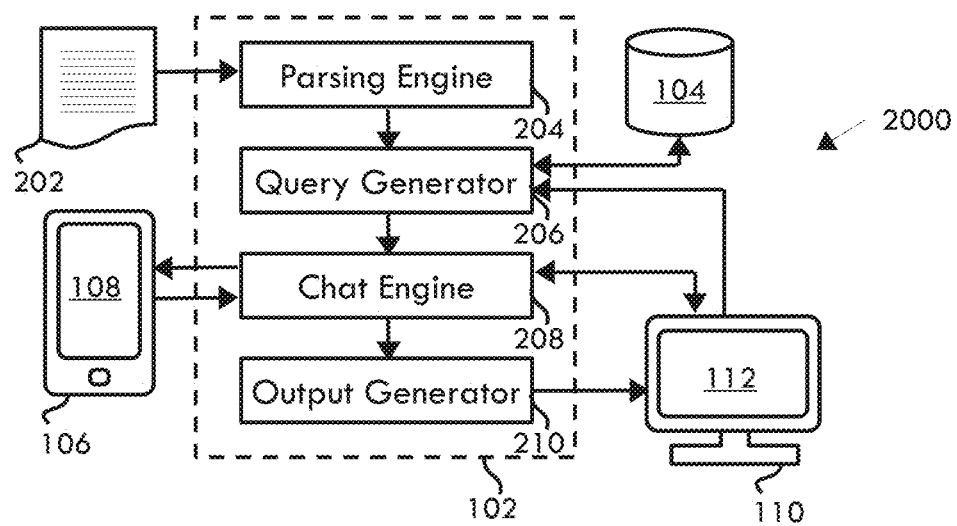
FIG. 2 illustrates a system for automated patient interaction according to a non-limiting embodiment.

FIG. 2 shows a system 2000 for automated patient interaction according to a non-limiting embodiment. The example illustrated in FIG. 2 illustrates components of the server computer 102 that may be implemented with hardware and/or software. For example, the server computer 102 may include a parsing engine 204, a query generator 206, a chat engine 208, and an output generator 210. Each of these components may be one or more software functions executable by the server computer 102 and/or may be part of one or several software applications. Moreover, it will be appreciated that one or more of the parsing engine 204, query generator 206, chat engine 208, and output generator 210 may be external to the server computer 102 and utilized as an external service. For example, the parsing engine 204 may be an external service that is called from the server computer 102 and returns one or more input vectors based on a complaint and/or patient data. Various other arrangements are possible.

With continued reference to FIG. 2, a complaint 202 is input into the parsing engine. The complaint 202 may include a textual description of a patient's symptoms, questions, and/or concerns that are initially presented by the patient (e.g., a chief complaint). The complaint 202 may be freeform text or may be structured data based on multiple inputs through a GUI. For example, the parsing engine may receive structured data, such as but not limited to JavaScript Object Notation (JSON) or XML, as input data for compatibility with one or more front-end web services (e.g., such as a client-side application or website) used to obtain input from the patient. The structured data may include, for example, several fields including a text string of the complaint, a value representing an age of the patient, a value representing a gender of the patient, and/or the like. In some non-limiting embodiments, the complaint 202 may be spoken into the first computing device 106 and a speech-to-text conversion may be performed by the first computing device 106 and/or the server computer 102.

Still referring to FIG. 2, in non-limiting embodiments, the parsing engine 204 may be configured to clean, normalize, and/or format the input text into a standardized and/or predetermined format using one or more Natural Language Processing (NLP) algorithms. The data format may be any type of data structure, such as a string with a standardized sentence, a vector formed from multiple substrings, and/or the like. In some non-limiting embodiments, the parsing engine 204 may output one or more vectors generated based on the complaint 202 and patient data. The vectors may be based on one or more words, phrases, and/or themes identified in the complaint 202 with the parsing engine. A non-limiting example of a vector 602 generated by the parsing engine 204 is shown in FIG. 6, where the input sentence (e.g., complaint) of "I have a cough and a fever" is used to generate a vector 602 in which each word in a vocabulary is represented by a TRUE (e.g., "1") or FALSE (e.g., "0") value. It will be appreciated that various formats of input vectors may be used in different non-limiting embodiments.

In non-limiting embodiments, the parsing engine 204 may employ word embedding techniques to generate a vector based on the complaint 202. For example, the vector 602 shown in FIG. 6 that represents the complaint 202 may be used to generate a further vector with a smaller vector space that takes into consideration the context of the words in the complaint, including adjacent words, ordering of words, and/or the like. Word embeddings may be based on a typical language dictionary (e.g., English) and/or may also be based on medical terminology. In some non-limiting embodiments, the word embeddings may be based on context within the complaint and/or from patient data. For example, a vector for the term "headache" may be a numerical representation that is adjusted based on one or more adjacent words in context. A full sentence of words may then be compressed into a single vector for use in the model. The parsing engine 204 may utilize any suitable algorithm to generate the vector such as, for example, a neural network, a probabilistic model, and/or the like.

Still referring to FIG. 2, the output of the parsing engine 204 is input to the query generator 206. The query generator 206 may include software and/or hardware configured to execute one or more algorithms to determine a subset of patient queries from numerous queries stored in the query database 104. For example, the query generator 206 may execute one or more algorithms that receive, as input, a feature vector based on the complaint 202 and patient data and output a subset of queries from the query database 104. The query generator 206 may employ one or more modeling and/or machine learning techniques to determine a subset of queries that correspond to the complaint and/or patient data (e.g., that are deemed to provide useful information related to the complaint) such as, for example, a neural network (e.g., a neural network, a convolutional neural network, or the like), a regression model (e.g., a logistic regression model, an elastic net regression model, or the like), a random forest model, a support-vector machine (SVM) model, and/or the like. The query generator 206 may utilize such models and/or machine-learning algorithms to identify correlations between the complaint 202 or portions thereof and queries from the query database 104. In non-limiting embodiments, the correlations may be a matter of degree such that the query generator 206 identifies the queries that are determined to be potentially relevant for the input to a threshold degree of confidence. The input to the query generator 206 may include one or more separate vectors for the complaint and the patient data or, in other examples, one or more vectors may be generated based on both the complaint and the patient data. Patient data may include, for example, age, gender, height, weight, medical history, and/or the like. It will be appreciated that various machine-learning algorithms may be implemented to determine an optimal subset of queries to present to the patient operating the first computing device 106. In non-limiting embodiments, the machine-learning algorithm may be configured to optimize for a minimum number of queries to present to the patient by learning which queries to skip in a given context to provide the same level of information to the clinician. In non-limiting embodiments, the machine-learning algorithm may employ multi-task learning to provide multiple outputs.

In non-limiting embodiments, the queries in the query database 104 may be categorized into one or more categories. For example, the query categories may include "story questions" (e.g., preliminary queries), asthma queries, dermatology queries, ear queries, fever/temperature queries, gastrointestinal queries, genital infection queries, headache/migraine queries, injury queries, medication queries, pain-related queries, mental health queries, respiratory queries, throat queries, urinary queries, vision queries, women's' health queries, and/or the like. In non-limiting embodiments, the query generator 206 may utilize a single model to determine queries from across multiple categories. In other non-limiting embodiments, the query generator 206 may utilize multiple models for multiple different query categories such that one or more categories has a corresponding model. The multiple models may or may not be dependent on one another. For example, an output from one model may be an input to another model or, in other examples, the models may operate independently.

In non-limiting embodiments, the query generator 206 may output the subset of queries as any form of structured data such as, for example, XML, JSON, and/or the like. The query generator 206 may also modify (e.g., adjust, edit, customize, and/or the like) one or more of the queries of the subset of queries based on the complaint 202 and/or patient data. An example output of the query generator 206 is shown in FIG. 7, where each query of a plurality of possible queries is represented in a vector 702 by a TRUE (e.g., "1") or FALSE (e.g., "0") value, such that the TRUE queries represent the subset of queries that are to be presented. It will be appreciated that various formats of outputs maybe used in different non-limiting embodiments.

Still referring to FIG. 2, in non-limiting embodiments, the chat engine 208 receives, as input, the subset of queries output by the query generator 206. As described above, the subset of queries may be in the form of structured data, such as but not limited to JSON or XML, compatible with any particular front-end web services (e.g., such as a client-side application or website) used to obtain responses from the patient. The chat engine 208 then communicates with the first computing device 106 to interact with the operator of the first computing device 106 (e.g., the patient or a user acting on behalf of the patient). The chat engine 208 may interact with the operator in real-time via text, audio, and/or video. As an example, the chat engine 208 may be a service provided by the server computer 102 that communicates individual queries to the first computing device 106 for display on a GUI 108 and receives responses from the first computing device 106 to those queries. In non-limiting examples, the chat engine 208 may be implemented with a modular web-based development framework, although any type of application and/or architecture may be used.

In non-limiting embodiments, the chat engine 208 may iterate through a structured hierarchy or graph of the subset of queries. In some non-limiting embodiments, the chat engine 208 may select a next query from the subset of queries, such as selecting a branch of a graph data structure, based on a previous response. In this manner only a portion of the subset of queries (e.g., a subset of the subset) may be asked depending on the responses received. This selection process may occur as a result of receiving a response that includes information responsive to multiple queries and/or a response that obviates presenting one or more other queries. For example, if a user responds "yes" to a particular query, the chat engine 208 may iterate through a portion of the subset of queries related to that initial query that would not be presented if the user responded "no" to that same query. Likewise, in other examples, if a user responds "no" to a particular query, the chat engine 208 may iterate through a portion of the subset of queries related to that initial query that would not be presented if the user responded "yes" to that query. In some non-limiting embodiments, each query of the subset of queries may be presented regardless of the responses.

In some non-limiting embodiments, the subset of queries may be determined by the query generator 206 on an ongoing basis during the interaction between the patient and the chat engine 208. For example, the query generator may initially output a first subset of queries that are presented with the chat engine 208, a second subset of queries that are based on the responses received to the first subset of queries, and so on with any number of subsets.

With continued reference to FIG. 2, the chat engine 208 may communicate with the second computing device 110 operated by a user, such as a clinician. The second computing device 110 may display a GUI 112 based on the interaction between the patient and the chat engine 208. For example, a clinician operating the second computing device 110 may view the dialog between the patient and the chat engine 208 in real-time and/or subsequent to it occurring. The second computing device 110 may also affect (e.g., influence) operation of the chat engine 208 by causing the chat engine 208 to include or skip one or more patient queries based on input received through the GUI 112. The clinician may also use the second computing device 110 to cause the chat engine 208 to stop automatically presenting queries. The clinician may then take over the interaction and begin communicating with the patient. The transition from the interaction provided by chat engine 208 to the interaction provided by the clinician through the second computing device 110 may be transparent to the patient or, in other examples, may be announced to the patient and made explicit.

Still referring to FIG. 2, in non-limiting embodiments, the chat engine 208 may output the queries and responses received to the queries to the output generator 210. For example, after automatically interacting with the operator of the first computing device 106, the chat engine 208 may output the responses and queries to the output generator 210 in any form. In some examples, the chat engine 208 may provide responses and queries to the output generator 210 on an ongoing basis as they are received. In other examples, the chat engine 208 may provide responses and queries to the output generator 210 after an automated patient interaction is complete. The output generator 210 generates one or more forms of structured data based on the queries and responses that are communicated to the second computing device 110. As an example, the output of the output generator may include one or more GUIs or portions thereof that display the queries and the patient's responses. The output may also include one or more recommendations, suggested follow-up queries, and/or the like.

With continued reference to FIG. 2, in non-limiting embodiments the query generator 206 is trained based on data received from the second computing device 110 and/or other computing devices (not shown in FIG. 2) in communication with the server computer 102. For example, a clinician may select one or more queries to skip, select one or more additional queries to include, select a priority of one or more queries, and/or the like, using selectable options displayed on the GUI 112 based on the output received from the output generator 210. This training data may be provided by the second computing device 110 before, during, and/or subsequent to a patient interaction and may include one or more inputs with respect to the queries and/or responses from the patient interaction such as, for example, removing one or more queries from the subset of queries, adding one or more queries to the subset of queries, editing one or more queries, merging one or more queries together, prioritizing one or more queries with respect to one or more other queries, deprioritizing one or more queries with respect to one or more other queries, ordering one or more queries (e.g., arranging a sequence or hierarchy of queries), and/or the like. In some non-limiting examples, multiple users of multiple computing devices, including the second computing device 110, may provide input for training purposes.

The user inputs received from the operator of the second computing device 110 and/or other computing devices are input to the query generator 206 to improve and optimize subsequent iterations. For example, one or more weights of one or more nodes in a neural network or other model may be adjusted based on selections from the clinician. In some non-limiting embodiments, the clinician's interaction with the patient may also be used to train the query generator 206. For example, additional queries asked by the clinician after the chat engine 208 has completed its interaction and/or additional inputs from the clinician to control or guide of the chat engine 208 during the interaction between the patient and chat engine 208 may be used to train the query generator 206 such that those additional queries may be identified in subsequent iterations. In non-limiting embodiments, such additional queries posed by the clinician may be used to train one or more rules for how queries are identified, presented, and/or relate to one another. In non-limiting embodiments, the additional queries posed by the clinician may be used to develop and/or design one or more GUIs (e.g., such as button placement, different types of options such as YES or NO, and/or the like).

Figure 3:
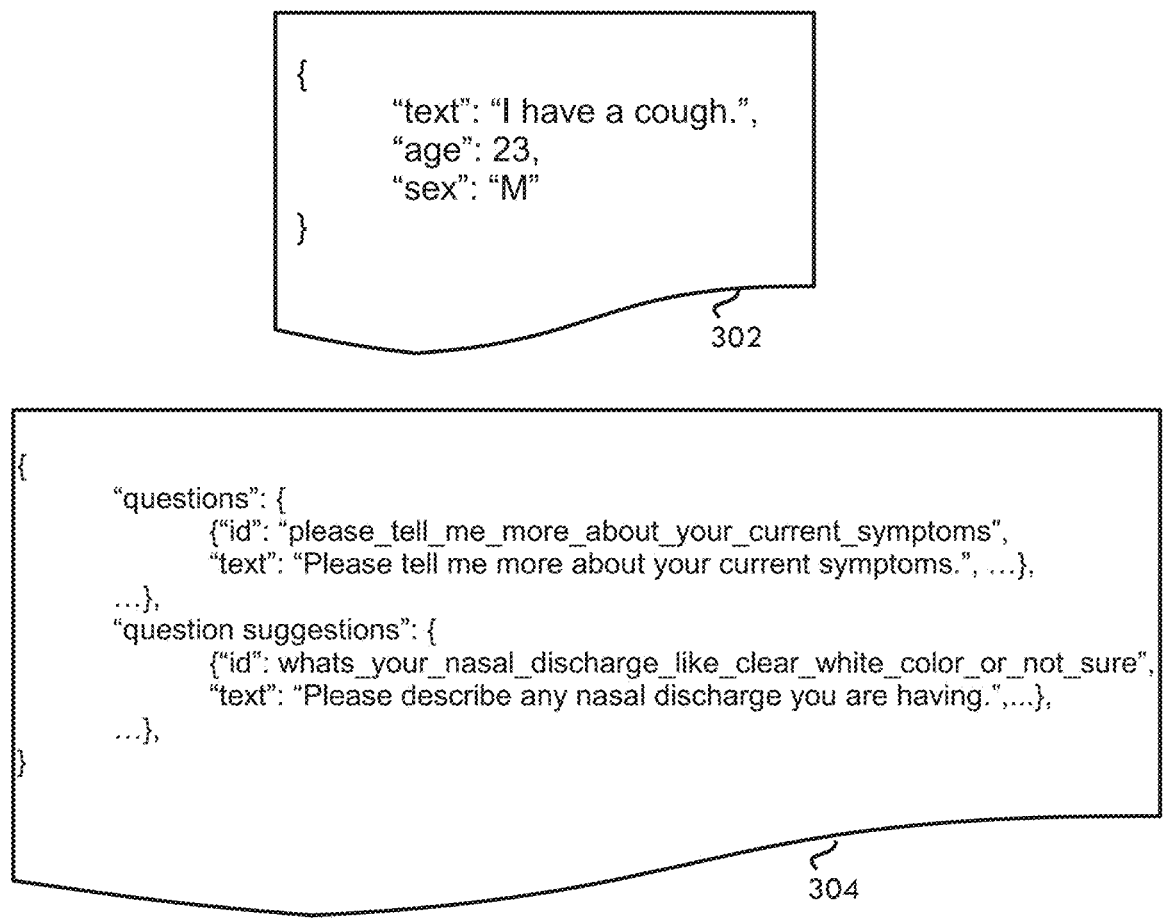
FIG. 3 illustrates structured data for use in a system for automated patient interaction according to a non-limiting embodiment.

Referring now to FIG. 3, structured data is shown for a patient input 302 (e.g., complaint data and patient data) and for a query output 304 (e.g., a subset of queries to be presented to the patient). Although the structured data shown in FIG. 3 is in JSON format, it will be appreciated that any structured data format may be used.

Referring now to FIGS. 4A and 4B, training GUIs 402, 404 are shown according to a non-limiting embodiment. The training GUIs 402, 404 include selectable options (e.g., buttons, checkboxes, radio buttons, input fields, links, and/or the like) for interaction with a user, such as a clinician. The training GUI 402 shown in FIG. 4A shows preliminary queries to ask based on a complaint (e.g., "I've had sinus pain for two weeks") and patient data (e.g., "26/Female"). Through the training GUI 402, a user selects preliminary queries that should be asked based on the complaint and patient data. The complaint may be an actual complaint that was received from a patient that was already interacted with or, in other examples, may be training data generated and/or obtained for the purpose of training. The training GUI 404 shown in FIG. 4B shows queries based on categories and selectable options for selecting one or more categories and/or queries from the categories. Through the training GUI 404, a user selects follow-up queries that should be asked based on the complaint, patient data, and, in some examples, responses received from the patient to the preliminary queries. The user selections received through the training GUIs 402, 404 are used to train the machine-learning model employed by the query generator. As explained herein, in some non-limiting embodiments, the machine-learning model may be trained based on actual queries presented to the patient by the clinician during and/or after the chat engine interaction.

Referring now to FIG. 5, a chat annotation GUI 502 is shown according to a non-limiting embodiment. The chat annotation GUI 502 may be used to train the machine-learning model and may be presented to one or more clinicians or other users after a patient interaction occurs and/or in real-time during the patient interaction. The chat annotation GUI 502 shows queries presented to the patient, responses to the queries, and selectable options for a user to select one or more labels to the patient responses. The labels may be any classifier such as tags, categories, keywords, and/or the like. In particular, a complaint 504 is displayed from an interaction and, next to the complaint 504, one or more labels 506 are displayed for selection by a user. The user may annotate the patient interaction by choosing and/or inputting one or more labels for each query/response pair. It will be appreciated that multiple users may annotate a patient interaction such that labels agreed upon by a majority of users may be utilized.

With continued reference to FIG. 5, the chat annotation GUI 502 may also display the queries 508 presented by the chat engine and, adjacent to each query, the responses 510 received to that query. One or more labels 512 may be displayed adjacent the queries 508 and responses 510 for selection by the user. The chat annotation GUI 502 may also display the queries 514 presented by the clinician after the automated patient interaction and, adjacent to each query, the responses 516 received to that query. One or more labels 518 may be displayed adjacent the queries 514 and responses 516 for selection by the user. It will be appreciated that the chat annotation GUI 502 may be arranged in various other ways.

Figure 8:
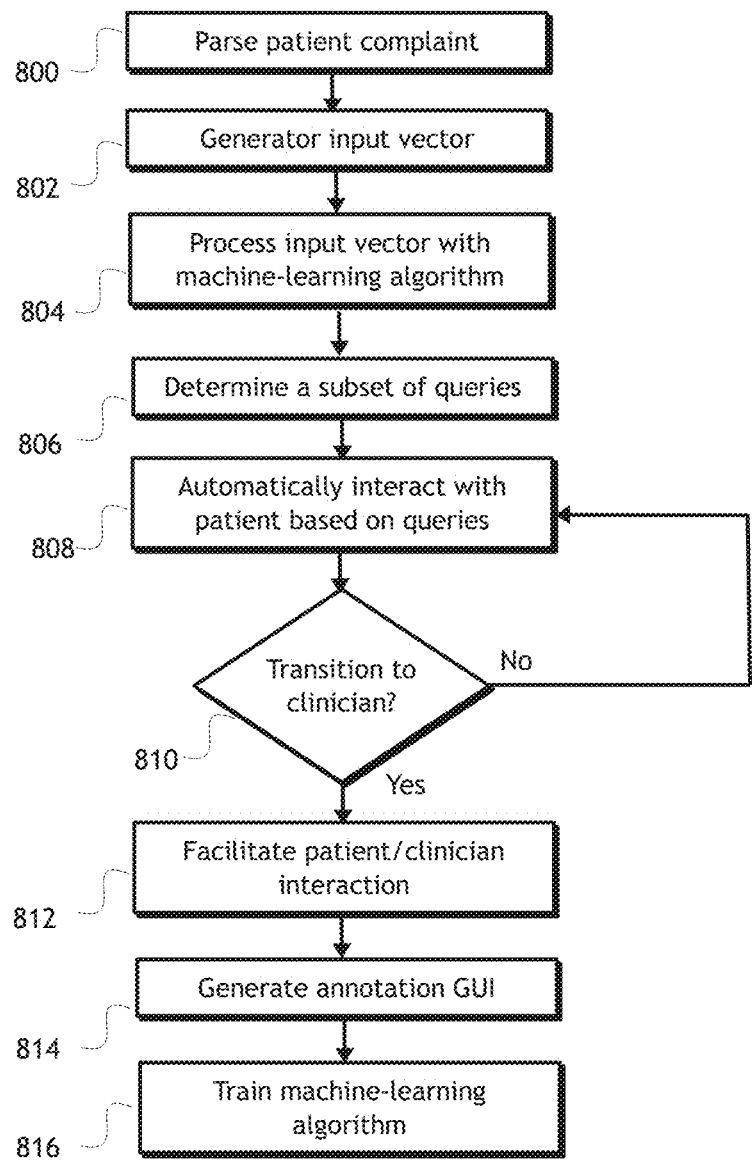
FIG. 8 illustrates a flow diagram for a system and method for automated patient interaction according to a non-limiting embodiment.

Referring now to FIG. 8, a flow diagram is shown for a system and method for automated patient interaction according to a non-limiting embodiment. It will be appreciated that the flow diagram is shown for exemplary purposes only and that the method may include fewer, additional, and/or different steps, and that the steps may be performed in any order. At step 800, a patient complaint is parsed. As explained herein, the patient complaint may be parsed with a parsing engine using one or more NLP algorithms. At step 802, an input vector is generated based on parsing the complaint and patient data related to the complaint. As explained herein, the input vector may be generated in various ways including, for example, word embedding techniques utilizing machine-learning algorithms. At step 804, the input vector is input into a machine-learning algorithm. As explained herein, the machine-learning algorithm may include a neural network, as an example, that correlates a subset of queries to a complaint and patient data (e.g., to an input vector based on a complaint and patient data). At step 806, a subset of queries is determined from a plurality of queries based on the machine-learning algorithm or other modeling technique.

With continued reference to FIG. 8, at step 808 an automated patient interaction is conducted based on the subset of queries determined at step 806. As explained herein, a chat engine may conduct an automated conversation with the patient to collect additional information. At step 810, it is determined whether the system should transition from the automated patient interaction conducted at step 808 to an interaction with a human operator (e.g., a clinician) at step 812. Various events may trigger the transition from the automated interaction to the clinician-driven interaction including, for example, input from the clinician stopping the automated interaction, the chat engine exhausting the subset of queries, a predetermined response from the patient, and/or the like. At step 812, interaction between the clinician and patient is facilitated. For example, the clinician may be presented with one or more GUIs for interacting with the patient to continue the conversation that was conducted with the chat engine at step 808.

Still referring to FIG. 8, after step 812 several steps (not shown in FIG. 8) may be performed by the clinician or other provider. For example, the clinician may provide a diagnosis, recommendation, and/or the like, to complete the encounter. After or during the encounter, one or more clinicians (including but not limited to the clinician that interacted with the patient at step 812) is presented with a chat annotation GUI at step 814 that allows the clinician or other user to provide input that is used to train the machine-learning algorithm (e.g., further train one or more models) at step 816. As explained herein, the machine-learning algorithm may also be trained at step 816 utilizing the follow-up queries and other inputs provided by the clinician at step 812 and/or during the automated interaction with the chat engine at step 808.

Figure 9:
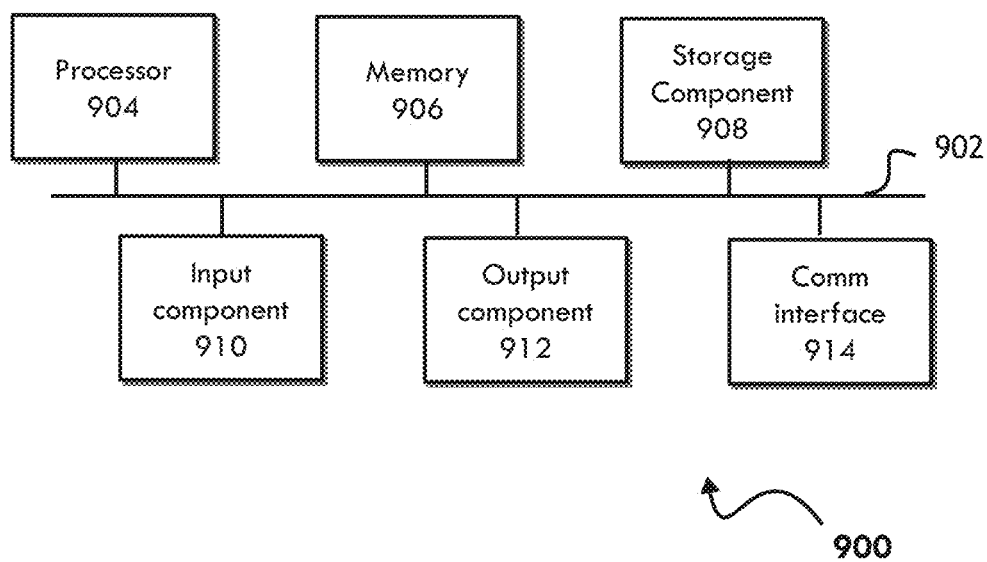
FIG. 9 illustrates example components of a computing device used in connection with non-limiting embodiments.

Referring now to FIG. 9, shown is a diagram of example components of a computing device 900 for implementing and performing the systems and methods described herein according to non-limiting embodiments. The computing device 900 may correspond to, for example, the first computing device 106, the second computing device 110, and/or the server computer 102. In some non-limiting embodiments, device 900 may include additional components, fewer components, different components, or differently arranged components than those shown in FIG. 9. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 9, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.).

Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A computer-implemented method for automated patient interaction, comprising:
    conducting, with at least one processor, an automated communication with a patient on a patient device based on a plurality of queries;
    collecting, with at least one processor, a plurality of responses from the patient via the patient device during the automated communication; and
    in response to a trigger event, transitioning the automated communication to a communication between the patient device and a clinician device by presenting at least one graphical user interface on the clinician device configured to facilitate the communication between the patient device and the clinician device, wherein transitioning from the automated communication to the communication occurs automatically in response to the trigger event, and wherein the trigger event comprises a clinician operating the clinician device communicating with an operator of the patient device.

2. The computer-implemented method of claim 1, wherein the trigger event comprises at least one of the following: input from the clinician device, exhaustion of the plurality of queries, receiving a predetermined response from the patient device, or any combination thereof.

3. The computer-implemented method of claim 1, wherein transitioning the automated communication to the communication between the patient device and the clinician device is transparent to the patient device.

4. The computer-implemented method of claim 1, wherein the communication between the patient device and the clinician device continues the automated communication.

5. The computer-implemented method of claim 1, further comprising:
    storing additional queries communicated by the clinician device to the patient device during the communication; and
    presenting at least one query of the additional queries during a subsequent automated communication with the patient or a different patient.

6. The computer-implemented method of claim 1, further comprising:
    receiving, from the clinician device, a selection of at least one of the following: one or more queries of the plurality of queries to skip, one or more additional queries to present during the automated communication, a priority of one or more queries of the plurality of queries, or any combination thereof, wherein the automated communication is conducted based on the selection.

7. A system for automated patient interaction, comprising:
    at least one processor in communication with at least one data storage device, the at least one processor programmed or configured to:
        conduct an automated communication with a patient on a patient device based on a plurality of queries;
        collect a plurality of responses from the patient via the patient device during the automated communication; and
        in response to a trigger event, transition the automated communication to a communication between the patient device and a clinician device by presenting at least one graphical user interface on the clinician device configured to facilitate the communication between the patient device and the clinician device, wherein transitioning from the automated communication to the communication occurs automatically in response to the trigger event, and wherein the trigger event comprises a clinician operating the clinician device communicating with an operator of the patient device.

8. The system of claim 7, wherein the trigger event comprises at least one of the following: input from the clinician device, exhaustion of the plurality of queries, receiving a predetermined response from the patient device, or any combination thereof.

9. The system of claim 7, wherein transitioning the automated communication to the communication between the patient device and the clinician device is transparent to the patient device.

10. The system of claim 7, wherein the communication between the patient device and the clinician device continues the automated communication.

11. The system of claim 7, wherein the at least one processor is further programmed or configured to:
  store additional queries communicated by the clinician device to the patient device during the communication; and
  present at least one query of the additional queries during a subsequent automated communication with the patient or a different patient.

12. The system of claim 7, wherein the at least one processor is further programmed or configured to:
  receive, from the clinician device, a selection of at least one of the following: one or more queries of the plurality of queries to skip, one or more additional queries to present during the automated communication, a priority of one or more queries of the plurality of queries, or any combination thereof, wherein the automated communication is conducted based on the selection.

13. A computer program product for automated patient interaction, comprising at least one non-transitory computer-readable medium including program instructions that, when executed by at least one processor, cause the at least one processor to:
  conduct an automated communication with a patient on a patient device based on a plurality of queries;
  collect a plurality of responses from the patient via the patient device during the automated communication; and
  in response to a trigger event, transition the automated communication to a communication between the patient device and a clinician device by presenting at least one graphical user interface on the clinician device configured to facilitate the communication between the patient device and the clinician device, wherein transitioning from the automated communication to the communication occurs automatically in response to the trigger event, and wherein the trigger event comprises a clinician operating the clinician device communicating with an operator of the patient device.

14. The computer program product of claim 13, wherein the trigger event comprises at least one of the following: input from the clinician device, exhaustion of the plurality of queries, receiving a predetermined response from the patient device, or any combination thereof.

15. The computer program product of claim 13, wherein the communication between the patient device and the clinician device continues the automated communication.

16. The computer program product of claim 13, wherein the at least one processor is further caused to:
  store additional queries communicated by the clinician device to the patient device during the communication; and
  present at least one query of the additional queries during a subsequent automated communication with the patient or a different patient.

17. The computer program product of claim 13, wherein the at least one processor is further caused to:
  receive, from the clinician device, a selection of at least one of the following: one or more queries of the plurality of queries to skip, one or more additional queries to present during the automated communication, a priority of one or more queries of the plurality of queries, or any combination thereof, wherein the automated communication is conducted based on the selection.

* * * * *